(12) United States Patent
Kurpad et al.

(10) Patent No.: US 8,805,475 B2
(45) Date of Patent: Aug. 12, 2014

(54) SYSTEM AND METHOD FOR TRACKING A POSITION OF AN INTERVENTIONAL MEDICAL DEVICE USING A MAGNETIC RESONANCE IMAGING SYSTEM

(71) Applicant: Wisconsin Alumni Research Foundation, Madison, WI (US)

(72) Inventors: Krishna N. Kurpad, Madison, WI (US); Madhav Venkateswaran, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 70 days.

(21) Appl. No.: 13/708,281

(22) Filed: Dec. 7, 2012

(65) Prior Publication Data

US 2014/0163355 A1      Jun. 12, 2014

(51) Int. Cl.
*A61B 5/055*   (2006.01)
*G01V 3/00*   (2006.01)

(52) U.S. Cl.
USPC ............ 600/411; 600/423; 600/424; 324/322

(58) Field of Classification Search
USPC ................... 600/411, 417, 422–424; 324/322
See application file for complete search history.

(56) References Cited

U.S. PATENT DOCUMENTS 8,082,041 B1   12/2011   Radziemski
2011/0007719 A1   1/2011   Lee
2011/0043210 A1   2/2011   Zimmerling et al.

OTHER PUBLICATIONS

Chandrakasan, et al., Ultralow-Power Electronics for Biomedical Applications, Annual Review of Biomedical Engineering, 2008, 10:247-274.

Gracias, et al., Antenna Operating Frequency Selection for Energy Harvesting on Nano Biomedical Devices, Proceedings of the 41st European Microwave Conference, 2011, pp. 64-66.

The Energy Harvesting Network, Energy Harvesting from Human Power: A Roadmap to New Research Challenges, Mar. 2011, 20 pages.

*Primary Examiner* — Michael Rozanski
(74) *Attorney, Agent, or Firm* — Quarles & Brady, LLP

(57) ABSTRACT

A system and method includes a medical device configured to be inserted into a subject having an imaging coil coupled thereto and configured to be inserted into the subject during a medical procedure to provide tracking information regarding a position of the medical device. A circuit is connected to the imaging coil to switch the circuit between an energy harvesting configuration and an image data acquisition configuration. The circuit includes an energy harvesting path and an imaging data path connected to the imaging coil that are electrically distinct. An energy storage device is connected to receive power delivered along the energy harvesting path when the circuit is in the energy harvesting configuration. An amplifier is connected to receive power from the energy storage device and receive imaging data signals from the imaging coil over the imaging data path to thereby amplify the imaging data signals.

21 Claims, 7 Drawing Sheets

SYSTEM AND METHOD FOR TRACKING A POSITION OF AN INTERVENTIONAL MEDICAL DEVICE USING A MAGNETIC RESONANCE IMAGING SYSTEM

STATEMENT REGARDING FEDERALLY SPONSORED RESEARCH

This invention was made with government support under HL086975 awarded by the National Institutes of Health. The government has certain rights in the invention.

BACKGROUND OF THE INVENTION

The present invention relates to systems and methods for magnetic resonance imaging ("MRI") and, more particularly, to systems and methods for tracking a position of a medical device designed for intervention into a subject using an MRI system.

When a substance such as human tissue is subjected to a uniform magnetic field (polarizing field $B_0$), the individual magnetic moments of the nuclear spins in the tissue attempt to align with this polarizing field, but process about it in random order at their characteristic Larmor frequency. Usually the nuclear spins are comprised of hydrogen atoms, but other NMR active nuclei are occasionally used. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$; also referred to as the radiofrequency (RF) field) which is in the x-y plane and which is near the Larmor frequency, the net aligned moment, $M_z$, may be rotated, or "tipped" into the x-y plane to produce a net transverse magnetic moment $M_t$, which is rotating, or spinning, in the x-y plane at the Larmor frequency. The practical value of this phenomenon resides in the signal which is emitted by the excited spins after the excitation field $B_1$ is terminated. There are a wide variety of measurement sequences in which this nuclear magnetic resonance ("NMR") phenomenon is exploited.

When utilizing these signals to produce images, magnetic field gradients ($G_x$, $G_y$, and $G_z$) are employed. Typically, the region to be imaged experiences a sequence of measurement cycles in which these gradients vary according to the particular localization method being used. The emitted MR signals are detected using a receiver coil. The MRI signals are then digitized and processed to reconstruct the image using one of many well-known reconstruction techniques.

The lack of ionizing radiation and the ability to provide anatomical images of soft tissue with sufficient resolution makes MRI an appealing modality to couple with interventional medical procedures that can be performed less invasively or more efficiently or safely when guided by MR images. For example, the guidance of therapeutic devices, such as catheters, and/or the placement of interventional devices, such as guidewires and stents, using MRI guidance is a promising and evolving field with great clinical potential.

One particular challenge of this field, however, has been how to develop safe and reliable methods for tracking such devices as they are moved and manipulated within vessels or organs. The tips of guidewires can be easily visualized using conventional x-ray fluoroscopy by applying small, radioopaque markers to the tips. Of course, x-ray fluoroscopy has the noted drawback of subjecting the patient and clinician to ionizing radiation. In MRI, the analog to the passive radio-opaque marker is a passive marker made of a material with a sufficiently large magnetic susceptibility, relative to the surrounding tissues, such as a stainless steel tip on a nitinol wire. In MR images depicting a guidewire containing such passive markers, a local hypointense region is present in the tissues adjacent to the markers, thereby resulting in a loss of clinically relevant information. Unfortunately, the high magnetic susceptibility of the material may induce artifacts in the MR images, among other drawbacks.

Accordingly, some other passive systems have been developed that have dedicated "indicator elements," for example, including a paramagnetic material. In such devices a paramagnetic material may be integrated with a catheter or other interventional medical device to influence the magnetic resonance image of a patient to be examined by means of an MRI system. The influence the device has on MR images makes it possible to determine the position of the interventional instrument within the body of the patient without the instrument being directly visible. However, the influence of the paramagnetic component in the device on the MR image adversely affects the diagnostic quality of the magnetic resonance image. As a result of the influence of the indicator element, MR images will exhibit degraded or lost anatomical details in the regions adjacent to the indicator element.

Despite being easy to locate in MR images and relatively inexpensive and safe, the aforementioned interventional devices produce a loss of signal or otherwise induce artifacts in the vicinity of the interventional device that, in turn, obscures the desired region of interest, namely, the tissue adjacent to the tip of the device. Thus, while the location of the tips of the aforementioned devices can be easily identified, the nature of the tissue that the devices are being moved through is obscured by the same effect that allows the visualization of the devices.

Accordingly, some active systems have been developed. For example, some catheters and other interventional devices have been coupled with local coils or other mechanisms that provide active feedback regarding the position of the interventional device. These systems have the advantage of providing real-time, controllable feedback acquired from the perspective of the interventional device that can be coupled with the general anatomical data acquired by the general imaging of the subject using the MR system and non-interventional coils.

Such internal, coil-based real-time MR-guided interventional devices struggle to achieve a sufficiently high intrinsic signal-to-noise ratio (SNR) necessary to overcome the challenges posed by the real-time data acquisition needed to guide the intervention. A major problem of internal MR receiver coils is the low radial visualization obtained due to the extremely small coil diameter. For example, in interventional applications, these local, internal coils struggle to achieve a sufficient field of view (FOV) to visualize clearly the position of the interventional device. While providing beneficial feedback, these local coils are prone to motion artifacts because when the imaged anatomy is moving, these coils will move with the anatomy, thereby resulting in blurred images.

Also, these active, coil-based systems that are integrated or coupled with the interventional device present a number of additional operational constraints on the clinician. For example, the internal coils are coupled to the MRI system or other external systems through a cable that extends from the tip of the interventional device, out of the patient, and to the external connection point. Micro-coaxial cables are typically used for such connections to transmit the signal from the internal coil to the external systems. Unfortunately, such micro-coaxial cables are very lossy, and inject a significant amount of thermal noise to the signal detected by the internal coil. This often means that smaller signals received by the internal coil, for example, such as received from regions at a distance from the internal coil, are indistinguishable from the noise injected along the connecting cable, resulting in further reduced radial coverage.

It would therefore be desirable to have a system and method for tracking interventional devices using MRI that does not obscure anatomical images acquired by the MRI system, has a sufficiently accuracy to allow precise tracking of the interventional device, and is acceptable to clinical settings.

SUMMARY OF THE INVENTION

The present invention overcomes the aforementioned drawbacks by providing a system and method for energy harvesting to drive and amplify MR signals received using an internal coil associated with an interventional medical device. The energy harvesting eliminates the requirement of an external power source. Instead, RF pulses from external RF coils associated with the MR system can be used as the source of power to drive the internal coil system for MR acquisition. The internal coil system for energy harvesting can be the same coil system as used to broadcast during the imaging cycle of the local coil. An amplification system can be included to amplify the received MR signal, for example, using the energy harvested. The amplification may be designed to drive broadcasting of the signal wirelessly, for example, using booster stages placed strategically along the interventional medical device or by simply broadcasting the signal to be picked up by the external MRI coil of the MRI system or other external systems. In this regard, the present invention can assist in reducing the number of cables running into the MRI scanner during an MR-guided interventional procedure.

In accordance with one aspect of the invention, a system is disclosed that is configured to be utilized with a magnetic resonance imaging system to perform an image-guided interventional medical procedure and a medical device configured to be inserted into a subject to perform a medical procedure. The system includes an imaging coil coupled to the medical device and configured to be inserted into the subject during the medical procedure to provide tracking information regarding a position of the medical device within the subject during the medical procedure and a circuit connected to the imaging coil and configured to switch between an energy harvesting configuration and an image data acquisition configuration. The circuit includes an energy harvesting path and an imaging data path connected to the imaging coil, wherein the energy harvesting path and the imaging data path are electrically distinct and an energy storage device connected to receive power delivered along the energy harvesting path when the circuit is in the energy harvesting configuration. The circuit further includes an amplifier connected to receive operational power from the energy storage device and receive imaging data signals from the imaging coil over the imaging data path to thereby amplify the imaging data signals when the circuit is in the imaging data acquisition configuration.

In accordance with another aspect of the invention, a magnetic resonance imaging (MRI) system is disclosed that includes a magnet system configured to generate a polarizing magnetic field about at least a portion of a subject arranged in the MRI system and a plurality of gradient coils configured to establish at least one magnetic gradient field to the polarizing magnetic field. The MRI system further includes a radio frequency (RF) system including an external imaging coil coupled to a transmit/receive switch configured to switch the system between applying an RF field to the subject during a transmit phase and receiving imaging signals from the subject during a receive phase. The MRI system also includes a medical device configured to be inserted into the subject to perform a medical procedure and an internal imaging coil coupled to the medical device and configured to be inserted into the subject during the medical procedure to provide tracking information regarding a position of the medical device within the subject during the medical procedure. The MRI system includes a circuit connected to the internal imaging coil and configured to switch between an energy harvesting configuration and an image data acquisition configuration. The circuit includes an energy harvesting path and an imaging data path connected to the internal imaging coil, wherein the energy harvesting path and the imaging data path are electrically distinct and an energy storage device connected to receive power delivered along the energy harvesting path when the circuit is in the energy harvesting configuration. The circuit also includes an amplifier connected to receive operational power from the energy storage device and receive imaging data signals from the internal imaging coil over the imaging data path to thereby amplify the imaging data signals when the circuit is in the imaging data acquisition configuration.

In accordance with yet another aspect of the invention, a method for performing an image guided interventional medical procedure is disclosed that includes arranging a subject within a magnetic resonance imaging (MRI) system including at least one external imaging coil arranged externally to the subject to acquire images of the subject using the at least one external imaging coil. The method also includes arranging a medical device, having associated therewith an imaging coil, inside the subject to acquire tacking information regarding a position of the medical device with the imaging coil associated with the medical device arranged within the subject while performing a medical procedure. When the MRI system is operating in a transmit mode to deliver radio-frequency (RF) energy to the subject using the at least one external imaging coil, the method includes harvesting the RF energy delivered to the subject by the at least one external imaging coil using the imaging coil associated with the medical device. When the MRI system is operating in a receive mode to acquire a medical imaging data signal from the subject using the at least one external imaging coil, the method includes receiving a medical imaging data signal from the subject using the imaging coil associated with the medical device. The method further includes using the energy harvested by the imaging coil associated with the medical device, at least one of amplifying and wirelessly transmitting the medical imaging data signal received by the imaging coil associated with the medical device.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
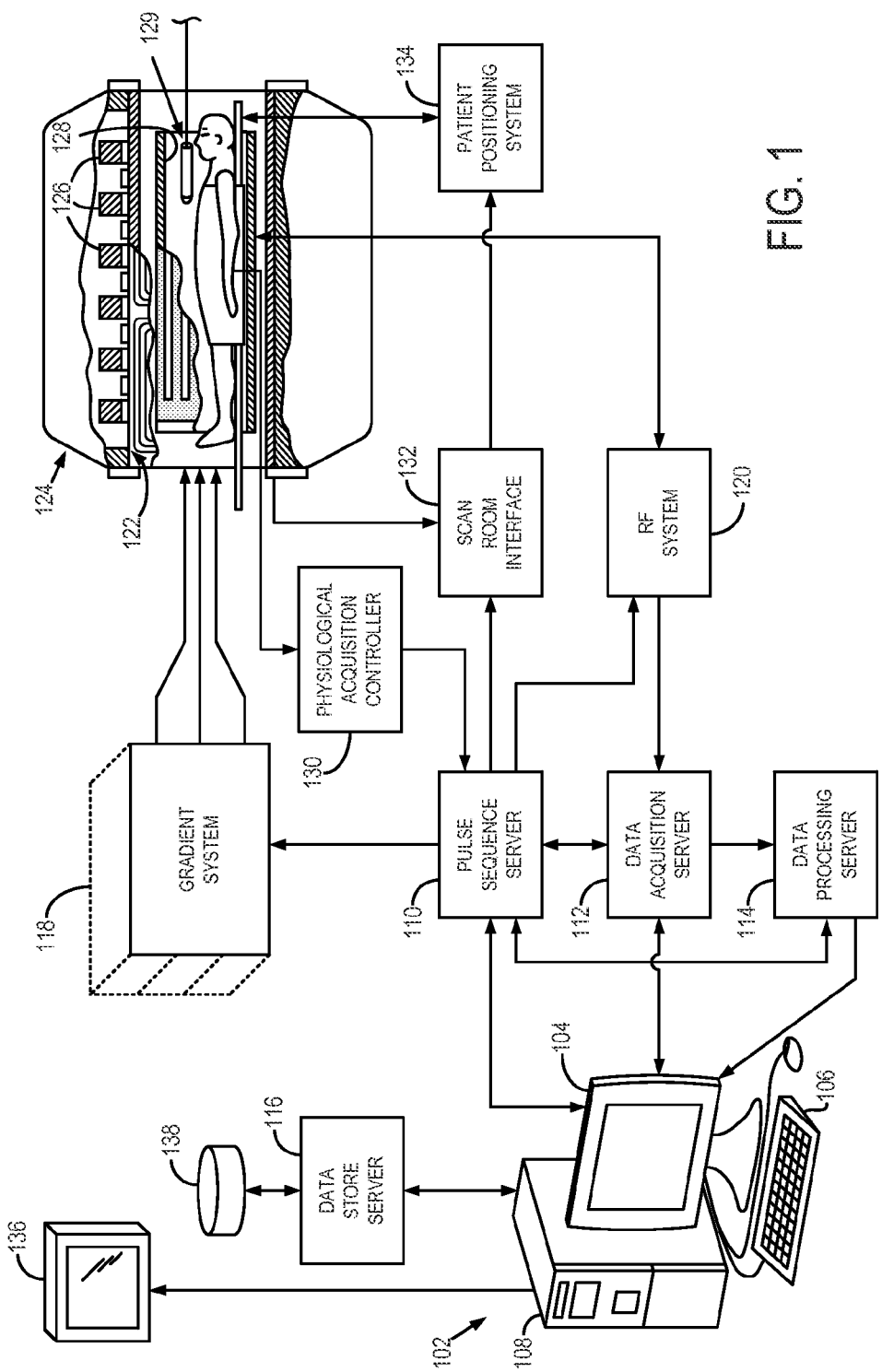
FIG. 1 is a block diagram of an example of a magnetic resonance imaging ("MRI") system.

Referring particularly now to FIG. 1, an example of a magnetic resonance imaging ("MRI") system 100 in accordance with the present invention is illustrated. The MRI system 100 includes a workstation 102 having a display 104 and a keyboard 106. The workstation 102 includes a processor 108, such as a commercially available programmable machine running a commercially available operating system. The workstation 102 provides the operator interface that enables scan prescriptions to be entered into the MRI system 100. The workstation 102 is coupled to four servers: a pulse sequence server 110; a data acquisition server 112; a data processing server 114; and a data store server 116. The workstation 102 and each server 110, 112, 114, and 116 are connected to communicate with each other.

The pulse sequence server 110 functions in response to instructions downloaded from the workstation 102 to operate a gradient system 118 and a radio frequency ("RF") system 120. Gradient waveforms used to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128.

RF excitation waveforms are applied by the RF system 120 to the RF coil 128 and/or, as will be described, a separate local coil that is associated with an interventional medical device 129, to perform the prescribed magnetic resonance pulse sequence. Responsive MR signals detected by the RF coil 128, or a separate local coil associated with the medical device 129, are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform.

The RF system 120 also includes one or more RF receiver channels. Each RF receiver channel includes an RF preamplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2}; \tag{1}$$

and the phase of the received MR signal may also be determined:

$$\varphi = \tan^{-1}\left(\frac{Q}{I}\right). \tag{2}$$

The pulse sequence server 110 also optionally receives patient data from a physiological acquisition controller 130. The controller 130 receives signals from a number of different sensors connected to the patient, such as electrocardiograph ("ECG") signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data are lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data are acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. In all these examples, the data acquisition server 112 acquires MR data and processes it in real-time to produce information that is used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

Figure 2:
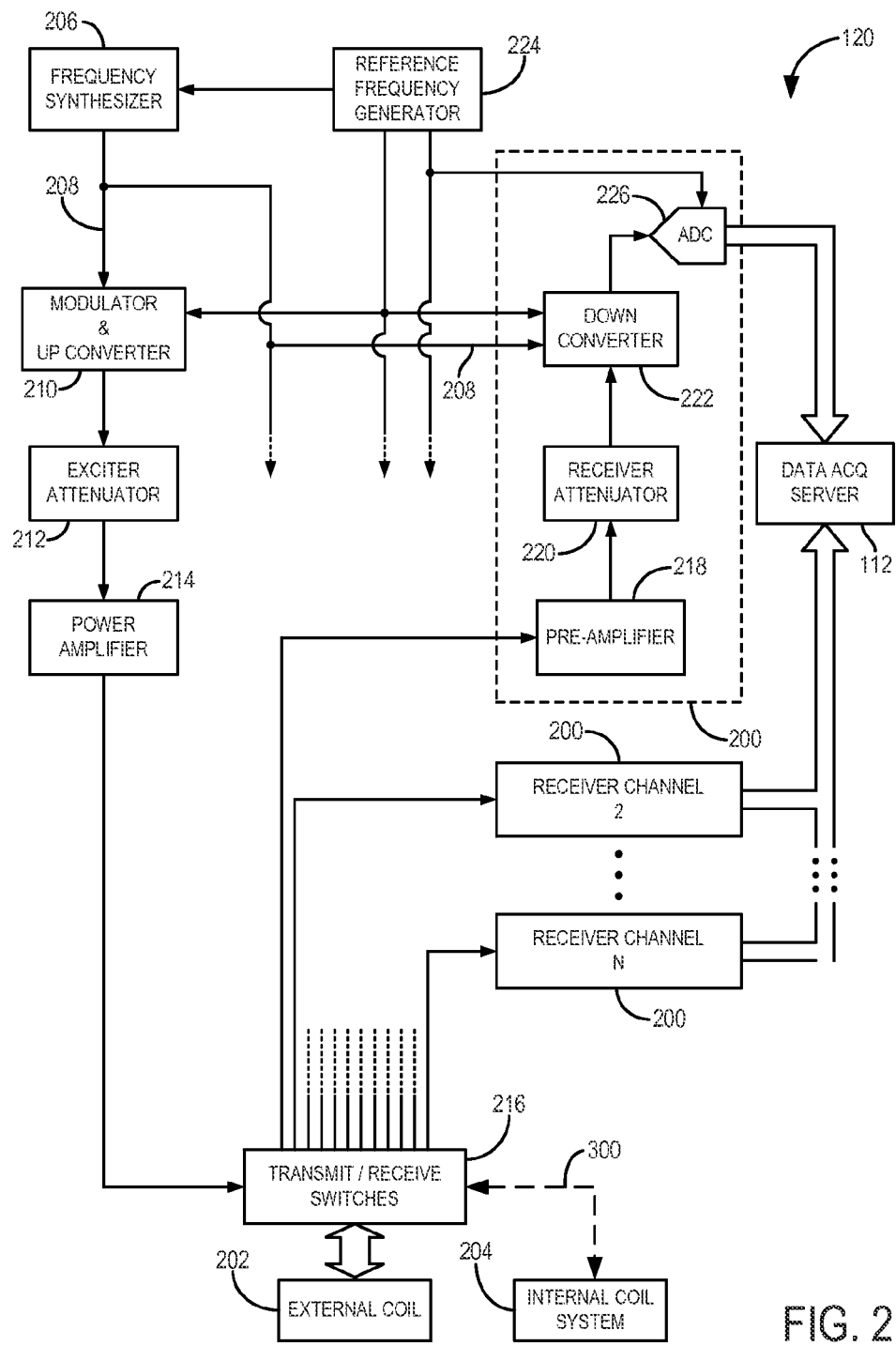
FIG. 2 is a block diagram of an example of a radio frequency ("RF") system that may form a part of the MRI system of FIG. 1.

As shown in FIG. 1, the RF system 120 may be connected to the whole body RF coil 128 and also a coil associated with the interventional medical device 129. Also, as shown in FIG. 2, a transmitter section of the RF system 120 may connect to at least one transmit channel 200 of an external coil 202 or internal coil 204. The external coil 202 may be the whole body RF coil 128 of FIG. 1 or a local transmit coil (not shown) and the internal coil 204 is, for example, the coil associated with the medical device 129 of FIG. 1, or other coil designed to be inserted into the patient being imaged, such as to facilitate high-resolution local imaging or image guided medical procedures.

Referring particularly to FIG. 2, the RF system 120 includes a transmitter system that produces a prescribed RF excitation field. The base, or carrier, frequency of this RF excitation field is produced under control of a frequency synthesizer 206 that receives a set of digital signals from the pulse sequence server 110 of FIG. 1. These digital signals indicate the frequency and phase of the RF carrier signal produced at an output 208. The RF carrier is applied to a modulator and up converter 210 where its amplitude is modulated in response to a signal, R(t), also received from the pulse sequence server 110 of FIG. 1. The signal, R(t), defines the envelope of the RF excitation pulse to be produced and is produced by sequentially reading out a series of stored digital values. These stored digital values may be changed to enable any desired RF pulse envelope to be produced.

The magnitude of the RF excitation pulse produced at output 208 is attenuated by an exciter attenuator circuit 212 that receives a digital command from the pulse sequence server 110 of FIG. 1. The attenuated RF excitation pulses are applied to a power amplifier 214, which drives the external coil 202 through a transmit/receive ("T/R") switch 216 and, as will be described, may be provided to the internal coil system 204.

Referring still to FIG. 2, the signal produced by the subject is picked up by the external coil 202 and applied to the inputs of a set of receiver channels 200. A pre-amplifier 220 in each receiver channel 200 amplifies the signal by an amount determined by a digital attenuation signal received from the pulse sequence server 110 of FIG. 1. The received signal is at or around the Larmor frequency, and this high frequency signal is down-converted in a two step process by a down converter 222, which first mixes the detected signal with the carrier signal on line 208 and then mixes the resulting difference signal with a reference signal from a reference frequency generator 224. The down converted MR signal is applied to the input of an analog-to-digital ("ND") converter 226 that samples and digitizes the analog signal and applies it to a digital detector and signal processor 228 that produces 16-bit in-phase (I) values and 16-bit quadrature (Q) values corresponding to the received signal. The resulting stream of digitized I and Q values of the received signal are output to the data acquisition server 112.

Figure 3:
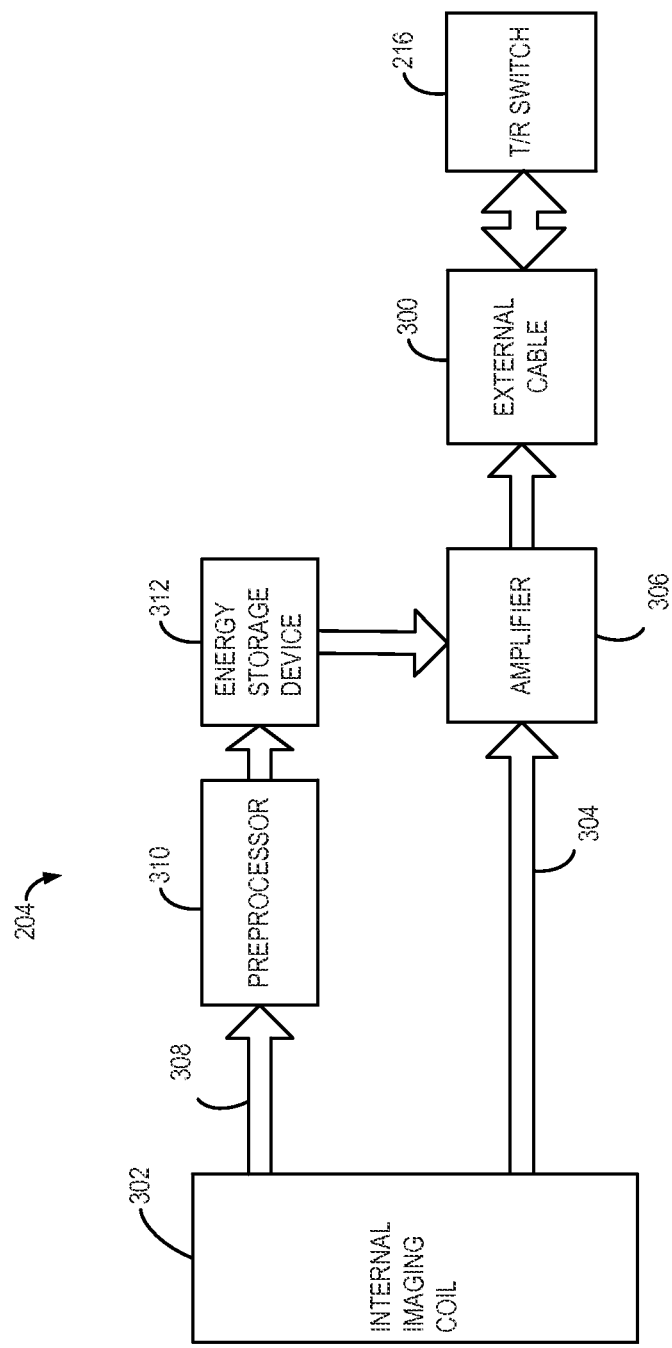
FIG. 3 is a schematic diagram of a system in accordance with the present invention.

Referring to FIG. 3, a schematic diagram of one particular implementation of the internal coil system 204 of FIG. 2 is illustrated. Specifically, FIG. 3 provides a schematic diagram of an implementation that uses an external cable 300 running from the internal coil system 204 to the external components of the MRI system or other systems. For example, the external cable 300 may connect the internal coil system 204 to the T/R switch 216 to, as will be described, switch the internal coil system 204 between receive and transmit cycles. In this way, the external cable 300 may connect the internal coil system 204 to a receiver channel 200 of the MRI system to communicate image data acquired by the internal coil system 204.

The internal coil system 204 includes an internal imaging coil 302. The internal imaging coil 302 is configured to perform two different forms of receive operations and, accordingly, has two different receive paths. Specifically, a first, imaging path or imaging receive path 304 is provided, that is designed to communicate MR imaging data signals acquired by the internal imaging coil 302 to an amplifier 306. A second, energy harvest or harvesting receive path 308 is provided to transmit energy harvested by the internal imaging coil 302 to a preprocessor 310 and storage device 312.

In operation, the internal coil system 204 and the greater MRI system, as external MR imaging coils, will coordinate operation. Specifically, during a transmit phase of MRI RF system and, thus, the external coil 202 of FIG. 2, the internal coil system 204 will operate in an energy harvesting state. To do so, the switch 216 causes the amplifier 306, which, as will be described, may be a transistor or similar discrete switch, to open the imaging receive path 304. As such, currents induced in the internal imaging coil 302 by the transmission of RF excitation pulses by external MR imaging coils will be directed along the harvesting receive path 308. The preprocessor 310, as will be described in further detail, is designed to condition the received power for storage in the energy storage device 312.

During the reception of imaging data, the switch 216 actuates such that the microvolt MR signals acquired by the internal imaging coil 302 are directed along the imaging receive path 304 to the amplifier 306. The amplifier 306 draws power from the energy storage device 312 to effectuate the amplification of the MR signals acquired by the internal imaging coil 302. Accordingly, as the MR signals travel along the external cable 300 to the MR system for processing and reconstruction, they are not overshadowed by noise injected along the external cable 300 because the amplified MR signals are amplified sufficiently above the microvolt level by the amplifier 306.

Figure 4:
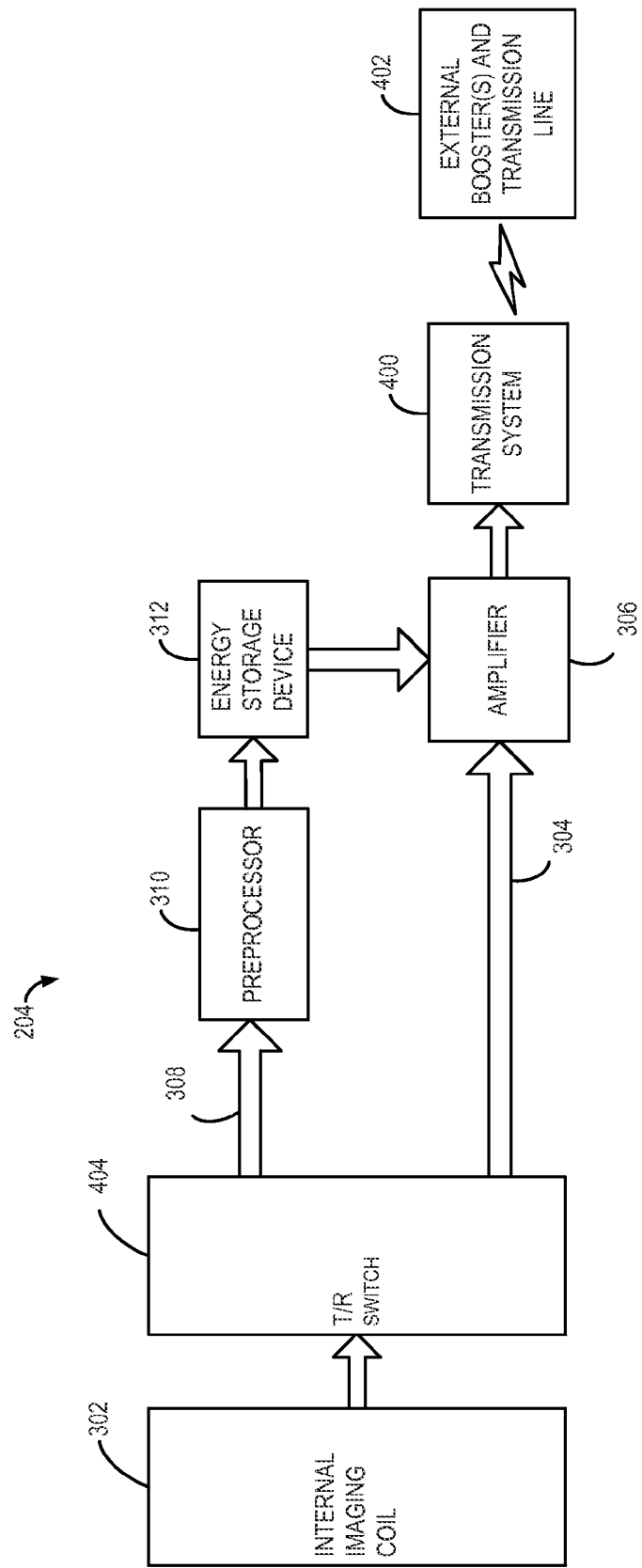
FIG. 4 is a schematic diagram of another system in accordance with the present invention.

Referring now to FIG. 4, the above-described internal coil system 204 may reduce the number of external cables entering the bore of the MRI system by, in accordance with this configuration, utilizing a plurality of transmitter/booster stages placed at strategic locations along the length of the medical device, such as a catheter, to which the internal imaging coil 302 is coupled. Specifically, as illustrated in FIG. 4, this configuration includes a transmission system 400 configured to wirelessly transmit the amplified MR signal to one or more boosters/repeater stages and/or an external transmission line 402 that, in turn, is connected to the MRI system. That is, a one or even a series of booster stages may be dispersed along the medical device and along a path to the MR system to receive the data communicated wirelessly by the transmission system 400 and then repeat the transmissions to, thereby, transmit the image data to the MRI system.

In this configuration, the use of the transmission system 400 removes the ability to use the switch 216 of the external MRI RF system to control operation of the internal coil system 204. As such, a switch 404 may be arranged between the internal imaging coil 302 and the imaging receive path 304 and harvesting receive path 308. In this way, the switch 404 coordinates operation between the phases of harvesting energy and receiving imaging data. To do so, the input impedance of the amplifier selected to be substantially small. Thus, the parallel capacitor and series inductors in the signal receive path forms a high impedance parallel resonant tank circuit on the input to the amplifier. So, during the transmit cycle, the diodes of the rectifier circuit are forward biased and charge the capacitor, forming a low impedance path to current sourced from the coil. During the receive cycle, the signal is sufficiently small so that the diodes block the flow of current. This results in the EMF appearing across the terminals of the tank circuit. The spin induced EMF drives a current in the tank circuit, which is then amplified by the MOSFET.

Figure 5:
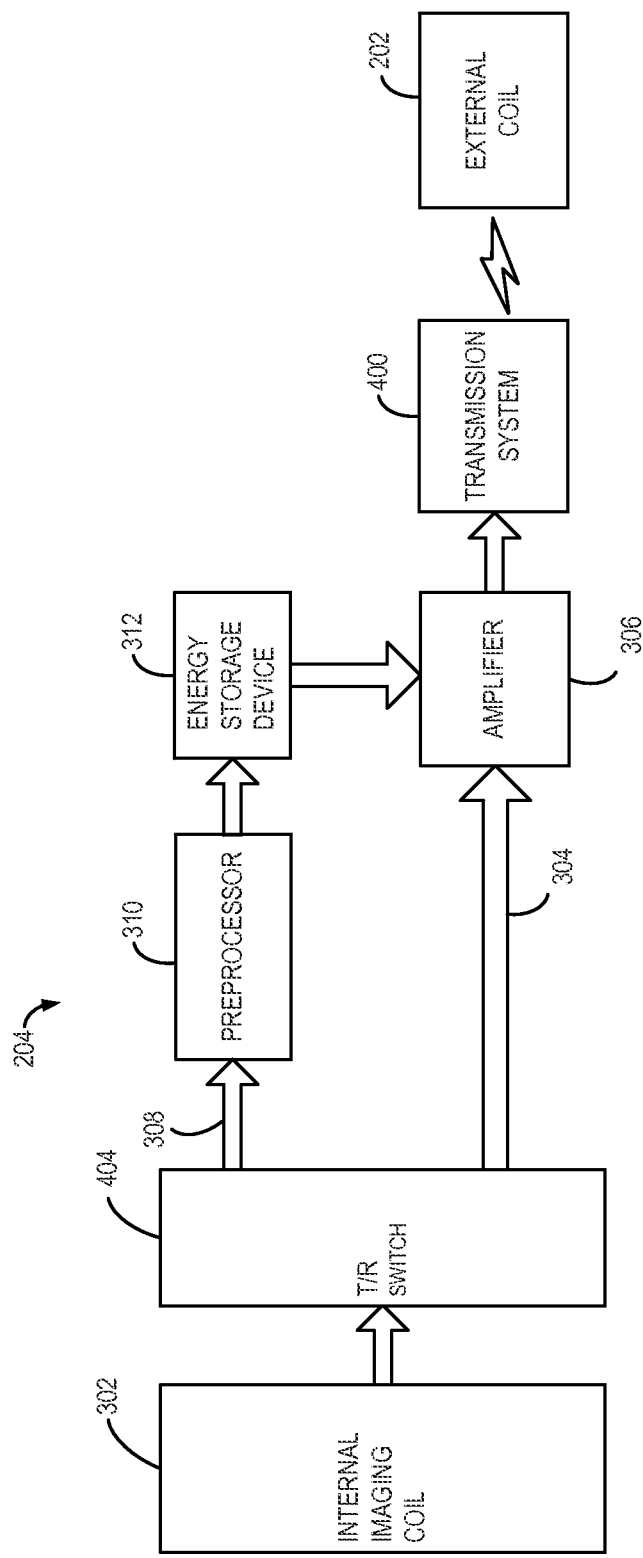
FIG. 5 is a schematic diagram of yet another system in accordance with the present invention.

Referring to FIG. 5, instead of using a transmission system 400 configured to wirelessly communicate data to external booster(s) and/or a transmission line 402, the transmission system 400 may be configured to wirelessly communicate image data to the external coil 202 of the MRI system. Specifically, the amplifier 306 drives the amplified signal into an integrated antenna, such as a micro-antenna. The integrated antenna then broadcasts the MR signal received by the internal imaging coil 302 to the external coil 202, which may be a transmit/receive coil or receive-only coil. The amplified signal from the internal imaging coil 302 is then superimposed on the MR signal acquired by the external coil 202 by the spins in the region of sensitivity of the internal imaging coil 302 and may, thus, be displayed as a region of enhanced signal within the FOV of the external coil.

Figure 6:
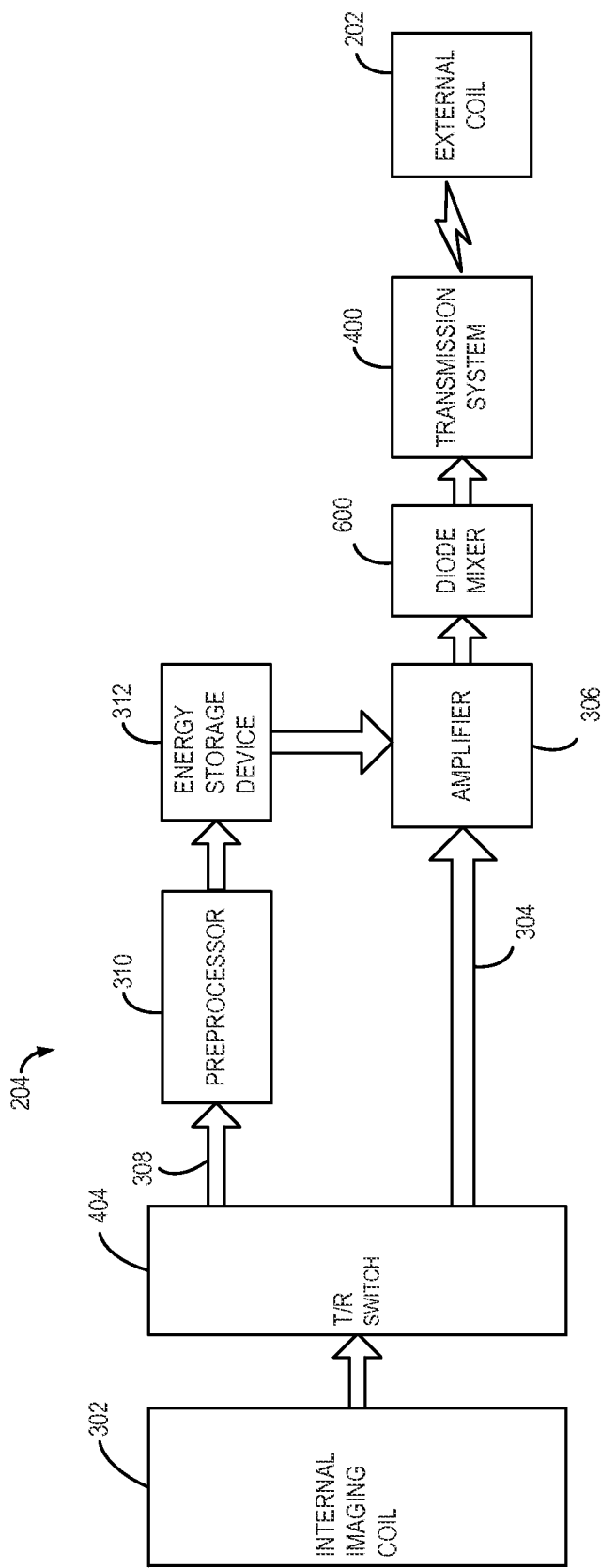
FIG. 6 is a schematic diagram of still another system in accordance with the present invention.

Referring to FIG. 6, the system of FIG. 5 may be further modified by inserting a diode mixer 600 to operate as a frequency doubler inserted into the signal path between the amplifier 306 transmission system 400. This configuration results in signal from the internal imaging coil 302 be adjusted, for example, having the frequency doubled or the signal phase shifted or otherwise modified. Accordingly, when the imaging data signal from the internal imaging coil 302 is transmitted by the transmission system 400 and received by the external coil 202, the modulated or adjusted characteristics of the internal imaging coil signal will be readily separable from imaging data acquired directly by the external coil 202. For example, if the imaging data signal from the internal imaging coil is frequency modulated, the separate signals received by the external coil 202 may be readily demodulated separately. In this example of frequency modulation, the external coil 202 is dual tuned to an imaging frequency, for example, 63.86 MHz, and the modulated frequency, such as 2× the imaging frequency. Alternatively, instead of a dual-tuned external coil 202, a second external coil may be used that is tuned to 2× the imaging frequency, or any other selected frequency.

Figure 7:
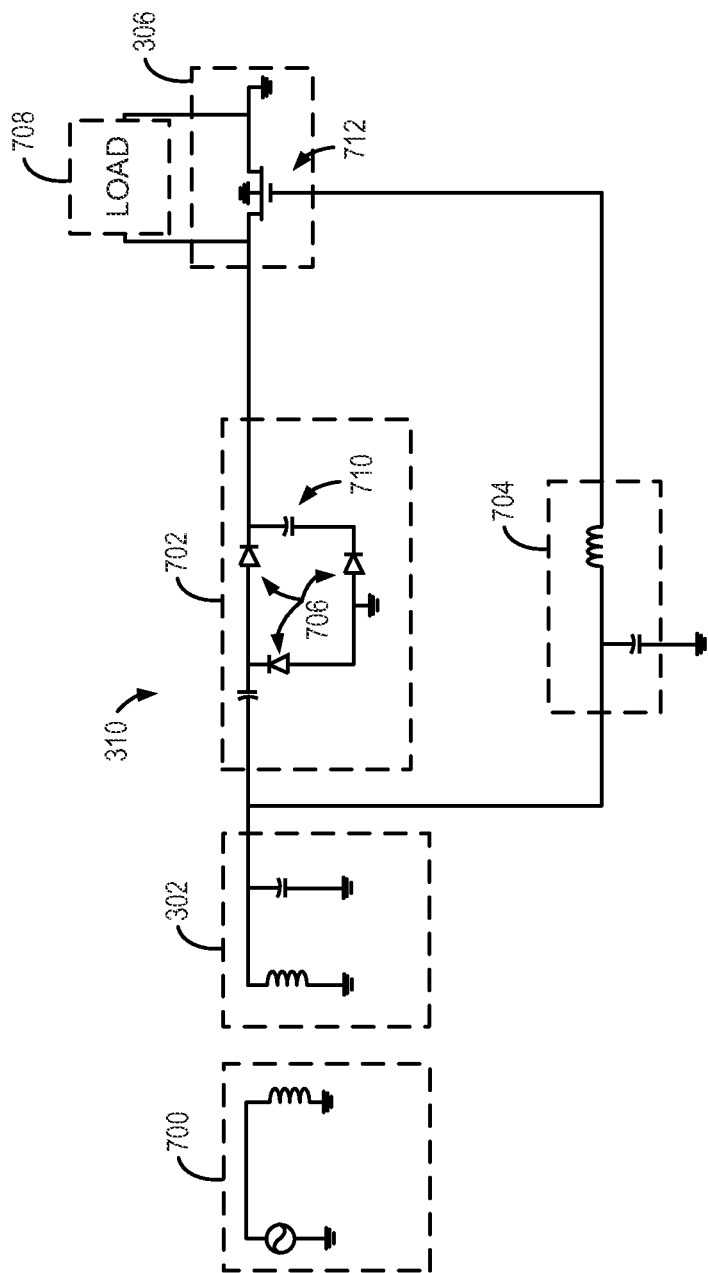
FIG. 7 is a schematic diagram of a circuit system for implementing the systems in accordance with the present invention.

Referring now to FIG. 7, one example of a circuit for the components of the internal coil system is illustrated. As illustrated, fundamental components of the afore-described internal coil system 204 are included. Specifically, the internal imaging coil 302, the preprocessor 310, the energy storage device 312, and the amplifier 306 are illustrated. As described above, additional components, such as switching and antennas may be added to these fundamental components.

Focusing on the components of the sub-circuits, the voltage generated by the internal receive coil 302 can be approximately calculated using Faraday's law for induced EMF, where:

$$V = -\frac{d\varphi}{dt};$$

and $$\Delta\varphi = BA = B_{1(rms)}(l*w).$$

For a 1.5T scanner, assuming a rectangular loop internal coil wound on a 6F catheter as the associated medical device, typical values of each of the parameters is given by:

$B_1$=20 uT, l=50 mm w=2 mm, f=63.86 MHz=>$\Delta t$=15.65 ns

Using these values, $$|V| = \frac{\Delta\varphi}{\Delta t} = \frac{B_{1(rms)}lw}{\Delta t} = 0.127 \text{ V}$$

This calculated value of induced voltage (order of 0.1V) gives an approximation to the voltage that may be available for rectification by the preprocessor 310. As can be seen 0.1V is a fairly small voltage and is challenging to use a 0.1V signal to power a transistor of the amplifier 306, such as the illustrated MOSFET. As will be described, a MOSFET is an advantageous transistor for some implementations; however, other suitable amplifiers, including other transistors BJTs, and the like, and non-transistor amplifiers may be utilized. One particular MOSFET, referred to as a "zero-threshold MOSFET," available from Advanced Linear Devices of California model ALD110800, may be advantageously utilized. Having a threshold voltage of 0.0V, these zero-threshold MOSFETs can be used as amplifiers at zero gate bias and a drain bias of only 0.1V and drawing 1 uA of drain-to-source current. By operating at a low DC voltage, these zero-threshold MOSFETS can be readily driven by the energy stored in the energy storage device 312 from the energy harvesting phase, even when the energy storage device primarily consists of a capacitor 704. Simulations show that voltages of higher amplitude may be generated given a sufficient length of time. Alternatively, a number of preparation RF pulses may be transmitted to fully charge the capacitor and be replenished during the execution of a pulse sequence.

As described above, the design of the circuit accommodates two operational phases. During the energy harvesting cycle, energy needs to be stored in the energy storage device 312, which can be modeled as a capacitor. This energy is used during the imaging data receive cycle in order to drive the amplifier 306 and achieve the desired amplification of the very small (order of uV) MR signal. The above-described switch systems, which may be implemented using diodes, switches between the two phases.

During a transmit phase of MRI RF system and, thus, the external coil 202 of FIG. 2, the internal coil system 204 will operate in an energy harvesting state. As illustrated in FIG. 7, during the transmit phase, the current induced in the coil 302 by mutual inductance with a transmit B1 filed 700, is transferred to a voltage rectifier circuit 702 as this presents a small impedance compared to the amplifier 306. That is, the amplifier 306 provides an high impedance in the following manner. For a low input impedance amplifier, a tank circuit 704 presents a high impedance to the coil 302, whereas the rectifier 702, particularly a set of diodes 706 of the rectifier 702, provides a low impedance, as they are forward biased. If the input impedance of the amplifier 306 is high, which is a less preferred design, then the tank circuit 704 may be omitted.

During the receive phase, the electromotive force (EMF) induced in the coil 302 by the spins is small and is not sufficient to forward bias the diodes 706 of the rectifier 702. Therefore, the rectifier 702 appears as an open circuit. The EMF appears across the tank circuit 704 and drives a current in the tank circuit 704. As the amplifier 306 can be conceptualized as part of the tank circuit 704, this current is amplified much like the well-known preamplifier decoupling technique employed in phased array receive coils. The amplified current is output to a load 708, which, as described above, can either be a cable or an antenna.

The above-described system can be implemented using a variety of specific circuit components. In the example illustrated in FIG. 7, the voltages harvested by the internal imaging coil 302 are fed through the rectifier 702, for example, a Greinecher rectifier, to then be stored in a main capacitor 710 or other component of the energy storage device 312.

The Greinecher voltage doubler is a well-known circuit to convert alternating AC power to a DC power of a value that is twice the voltage of the peak AC value. A two-stage Greinecher voltage doubler can readily convert 0.1V AC to a steady-state DC output voltage of approximately to 0.15V, using R-C values chosen to obtain a desired time constant value for the MR frequency of 63.86 MHz.

During the receive cycle of MRI RF system, the above-described switching systems will cause the amplifier 306 to be turned on. As illustrated, the amplifier 306 may include a MOSFET transistor 712 powered by the stored energy in the main capacitor 710. The MOSFET transistor 712 amplifies the MR signal received by the internal imaging coil 302 and delivers it to the desired load 708. The load 708 in the illustrated circuit is a placeholder for the above-described systems for communicating the acquired imaging data to the external systems for the MRI system. As described above, these may include an external cable, wireless transmitters/boosters, antennas, and the like.

The choice of R-C values at every stage of the circuit is important in determining the charging up and discharging time constants so as to achieve optimum amplification of the MR signal. In the illustrated example where the amplifier 306 includes a MOSFET 712, switching to perform harvesting presents low resistance as seen at a drain output of the MOSFET 712, where the load 708 is connected. Thus, when in the energy harvesting phase, current flows away from the amplifier 306 and the amplifier 306 remains switched off. However, the RC time constant of the switch-output capacitor combination should be much larger than the RC time constant of the coil-output capacitor combination. This ensures that the capacitor is charged much faster than it is being discharged, implying that while the resistance as seen at the load 708 connected to the amplifier 306 must be smaller than the off-resistance of the MOSFET 712, it must be larger than the resistance of the internal imaging coil 302 (output capacitor remains constant).

During the reception of imaging data, the resistance as seen at the load 708 should be large so that the entire current is driven through the amplifier 306, thus turning the MOSFET 712 on. The input signal is coupled to the gate and the amplified output is obtained as a voltage signal at the load 708. A typical MR signal picked up by the internal imaging coil 302 is of the order of a microvolt.

It can be seen that during energy harvesting phase, the output signal may be only of the order of 5 mV, despite the large 0.1V input signal as against the 1 uV input signal during the imaging receive phase. On the other hand, during the imaging receive phase, the signal is on the order of 50 mV. This represents an attenuation of the transmit signal by 32 dB, and an amplification of the MR signal during the receive phase by approximately 83 dB. This indicates that the amplifier 306 is turned off during harvesting phase, while the stored energy in the capacitor 712 drives the amplifier 306 during the receive phase, achieving signal amplification. Looking at the signal at the MR frequency of 63.86 MHz, the amplified output signal during the receive phase is about 15 dB (−37 dB as compared to −52 dB) higher than the signal during the transmit phase, demonstrating the feasibility of capturing only the signal of interest.

Thus, the present invention overcomes the aforementioned drawbacks by providing a system and method for energy harvesting to drive and amplification of MR signals received using an internal coil associated with an interventional medical device. The energy harvesting eliminates the requirement of an external power source. Instead, RF pulses from external RF coils associated with the MR system can be used as the source of power to drive the internal coil system for MR acquisition. The internal coil system for energy harvesting can be the same coil system as used to excite nuclear spins during the transmit/receive imaging cycle of the local coil. An amplification system can be included to amplify the received MR signal, for example, using the energy harvested. The amplification may be designed to drive transmission of the signal wirelessly, for example, using booster stages placed strategically along the interventional medical device or by simply transmitting the signal to be picked up by the external MRI coil of the MRI system or other external systems. In this regard, the present invention can assist in reducing the number of cables running into the MRI scanner during an MR-guided interventional procedure.

The present invention has been described in terms of one or more preferred embodiments, and it should be appreciated that many equivalents, alternatives, variations, and modifications, aside from those expressly stated, are possible and within the scope of the invention.

The invention claimed is:

1. A system configured to be utilized with a magnetic resonance imaging system to perform an image-guided interventional medical procedure, the system comprising:
   a medical device configured to be inserted into a subject to perform a medical procedure;
   an imaging coil coupled to the medical device and configured to be inserted into the subject during the medical procedure to provide tracking information regarding a position of the medical device within the subject during the medical procedure;
   a circuit connected to the imaging coil and configured to switch between an energy harvesting configuration and an image data acquisition configuration, the circuit comprising:
      an energy harvesting path and an imaging data path connected to the imaging coil, wherein the energy harvesting path and the imaging data path are electrically distinct;
      an energy storage device connected to receive power delivered along the energy harvesting path when the circuit is in the energy harvesting configuration; and
      an amplifier connected to receive operational power from the energy storage device and receive imaging data signals from the imaging coil over the imaging data path to thereby amplify the imaging data signals when the circuit is in the image data acquisition configuration.

2. The system of claim 1 further comprising a processing component coupled between the energy harvesting path and the energy storage device to condition power received by the imaging coil when the circuit is in the energy harvesting configuration for storage by the energy storage device.

3. The system of claim 1 further comprising a switching system configured to switch the circuit between the energy harvesting configuration and the image data acquisition configuration.

4. The system of claim 3 wherein the switching system is configured to coordinate switching the circuit between the energy harvesting configuration and the image data acquisition configuration with operation of an MRI system.

5. The system of claim 3 wherein the switching system is configured to switch the circuit into the energy harvesting configuration when an MRI system performing an imaging process of the subject is in a transmit phase and switch the circuit into the image data acquisition configuration when the MRI system is in a receive phase.

6. The system of claim 4 wherein the switching system includes a transmit/receive switch of the MRI system.

7. The system of claim 1 further comprising a transmission system configured to wirelessly transmit amplified imaging data signals from a location inside the subject to a location externally to the subject.

8. The system of claim 7 wherein the transmission system includes at least one of a series of boosters configured to relay the amplified imaging data signals to the location externally to the subject and an antenna configured to transmit the amplified imaging data signals for receipt by an imaging coil of the MRI system located externally from the subject.

9. The system of claim 1 further comprising a modulation component configured to adjust a characteristic of the imaging data signals to be distinguishable from imaging data signals acquired from the subject by coils other than the imaging coil coupled to the medical device.

10. The system of claim 9 wherein the characteristic of the imaging data signals includes at least one of amplitude, frequency, and phase.

11. A magnetic resonance imaging (MRI) system, comprising:
a magnet system configured to generate a polarizing magnetic field about at least a portion of a subject arranged in the MRI system;
a plurality of gradient coils configured to establish at least one magnetic gradient field to the polarizing magnetic field;
a radio frequency (RF) system including an external imaging coil coupled to a transmit/receive switch configured to switch the system between applying an RF field to the subject during a transmit phase and receiving imaging signals from the subject during a receive phase;
a medical device configured to be inserted into the subject to perform a medical procedure;
an internal imaging coil coupled to the medical device and configured to be inserted into the subject during the medical procedure to provide tracking information regarding a position of the medical device within the subject during the medical procedure;
a circuit connected to the internal imaging coil and configured to switch between an energy harvesting configuration and an image data acquisition configuration, the circuit comprising:
an energy harvesting path and an imaging data path connected to the internal imaging coil, wherein the energy harvesting path and the imaging data path are electrically distinct;
an energy storage device connected to receive power delivered along the energy harvesting path when the circuit is in the energy harvesting configuration; and
an amplifier connected to receive operational power from the energy storage device and receive imaging data signals from the internal imaging coil over the imaging data path to thereby amplify the imaging data signals when the circuit is in the image data acquisition configuration.

12. The system of claim 11 wherein the circuit further comprises a processing component coupled between the energy harvesting path and the energy storage device to condition power received by the internal imaging coil when the circuit is in the energy harvesting configuration for storage by the energy storage device.

13. The system of claim 11 wherein the circuit further comprises a switching system configured to switch the circuit between the energy harvesting configuration and the image data acquisition configuration.

14. The system of claim 13 wherein the switching system is configured to switch the circuit into the energy harvesting configuration when the transmit/receive switch has configured the RF system in the transmit phase to apply an RF field to the subject and the switching system is configured to switch the circuit into the image data acquisition configuration when the transmit/receive switch has configured the RF system in the receive phase to receive imaging signals from the subject.

15. The system of claim 13 wherein the switching system is arranged between the internal imaging coil and the energy harvesting path and the imaging data path.

16. The system of claim 11 further comprising a transmission system configured to wirelessly transmit amplified imaging data signals from a location inside the subject to the MRI system.

17. The system of claim 16 wherein the transmission system includes at least one of a series of boosters configured to rely the amplified imaging data signals to the MRI system and an antenna configured to transmit the amplified imaging data signals for receipt by the external imaging coil of the MRI system.

18. The system of claim 11 further comprising a modulation component configured to adjust a characteristic of the imaging data signals to be distinguishable from imaging data signals acquired by the external imaging coil of the MRI system.

19. The system of claim 18 wherein the characteristic includes one of an amplitude, a frequency, and a phase of the imaging data signals acquired by the internal imaging coil.

20. A method for performing an image guided interventional medical procedure, the method comprising:
arranging a subject within a magnetic resonance imaging (MRI) system including at least one external imaging coil arranged externally to the subject to acquire images of the subject using the at least one external imaging coil;
arranging a medical device, having associated therewith an imaging coil, inside the subject to acquire tacking information regarding a position of the medical device with the imaging coil associated with the medical device arranged within the subject while performing a medical procedure;
when the MRI system is operating in a transmit mode to deliver radio-frequency (RF) energy to the subject using the at least one external imaging coil, harvesting the RF energy delivered to the subject by the at least one external imaging coil using the imaging coil associated with the medical device;
when the MRI system is operating in a receive mode to acquire a medical imaging data signal from the subject using the at least one external imaging coil, receiving a medical imaging data signal from the subject using the imaging coil associated with the medical device; and
using the energy harvested by the imaging coil associated with the medical device, at least one of amplifying and wirelessly transmitting the medical imaging data signal received by the imaging coil associated with the medical device.

21. The method of claim 20 further comprising adjusting at least one of an amplitude, a phase, and a frequency of the medical imaging data signal received by the imaging coil associated with the medical device for transmission to the MRI system in a manner distinguishable from the medical imaging data signal acquired from the subject using the at least one external imaging coil.

* * * * *

UNITED STATES PATENT AND TRADEMARK OFFICE
CERTIFICATE OF CORRECTION

PATENT NO. : 8,805,475 B2
APPLICATION NO. : 13/708281
DATED : August 12, 2014
INVENTOR(S) : Krishna N. Kurpad and Madhav Venkateswaran It is certified that error appears in the above-identified patent and that said Letters Patent is hereby corrected as shown below:

In the Specification

Column 1, line 23 "process" should be --precess--

Signed and Sealed this
Fourteenth Day of June, 2016

Michelle K. Lee
*Director of the United States Patent and Trademark Office*